(12) United States Patent
Kim et al.

(10) Patent No.: US 11,197,726 B2
(45) Date of Patent: Dec. 14, 2021

(54) MICROROBOTIC TENTACLES WITH SPIRAL BENDING CAPABILITY BASED ON SHAPE-ENGINEERED ELASTOMERIC MICROTUBES AND METHODS OF MANUFACTURING SAME

(71) Applicants: Jaeyoun Kim, Ames, IA (US); In Ho Cho, Ames, IA (US); Jungwook Paek, Philadelphia, PA (US)

(72) Inventors: Jaeyoun Kim, Ames, IA (US); In Ho Cho, Ames, IA (US); Jungwook Paek, Philadelphia, PA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1096 days.

(21) Appl. No.: 15/342,829

(22) Filed: Nov. 3, 2016

(65) Prior Publication Data
US 2017/0129111 A1 May 11, 2017

Related U.S. Application Data

(60) Provisional application No. 62/251,725, filed on Nov. 6, 2015.

(51) Int. Cl.
*A61B 34/30* (2016.01)
*A61B 17/00* (2006.01)

(52) U.S. Cl.
CPC .... *A61B 34/30* (2016.02); *A61B 2017/00526* (2013.01); *A61B 2017/00544* (2013.01)

(58) Field of Classification Search
CPC .............................. B29C 33/52; B29C 41/14
See application file for complete search history.

(56) References Cited

U.S. PATENT DOCUMENTS

| 6,076,212 A * | 6/2000 | Feld ..................... A47C 19/021 5/424 |
| 2005/0044715 A1* | 3/2005 | Shutts .................. G02B 6/4497 30/90.1 |

(Continued)

FOREIGN PATENT DOCUMENTS

WO   WO2014/022667 A2 *   2/2014

OTHER PUBLICATIONS

Kamiya et al., "Micro tube manufacturing method of tube-shaped dilation micromanipulator made of shape memory polymer", ASPE 2004 Annual Conference, available at https://web.archive.org/web/20100715172713/https://aspe.net/publications/Annual_2004/posters/2equip/5mems/1602.pdf captured on Jul. 15, 2010 (Year: 2010).*

(Continued)

*Primary Examiner* — Galen H Hauth
(74) *Attorney, Agent, or Firm* — Reinhart Boerner Van Deuren P.C.

(57) ABSTRACT

Elastomer-based soft-robotic micro-tentacles capable of winding around and holding microscale objects and methods of fabricating same are provided. To realize the thin, highly deformable microtubes, a fabrication technique based on in situ thermal solidification of PDMS dip-coated around a cylindrical template and direct peeling of the cured structure is presented. This process is capable to asymmetrize the microtube's cross-sectional shape and enable the microtube to bend up to a single turn. To amplify the bending into a life-like, multi-turn spiraling motion, a semi-analytical model to shape-engineer the microtube and turn it into a micro-tentacle was produced. As a result, a hump is added to the microtube to enable the multi-turn spiraling motion.

17 Claims, 5 Drawing Sheets

(56) References Cited

U.S. PATENT DOCUMENTS

| | | | | |
|---|---|---|---|---|
| 2006/0070167 | A1* | 4/2006 | Eng | A61K 8/345 |
| | | | | 2/168 |
| 2007/0020388 | A1* | 1/2007 | Huang | B29D 11/00865 |
| | | | | 427/162 |
| 2012/0071553 | A1* | 3/2012 | Doyle | A23F 3/163 |
| | | | | 514/517 |
| 2013/0172993 | A1* | 7/2013 | Yu | B29C 41/14 |
| | | | | 623/8 |
| 2014/0144994 | A1* | 5/2014 | Conner | G06K 19/07783 |
| | | | | 235/492 |
| 2014/0332997 | A1* | 11/2014 | Shih | B29C 41/42 |
| | | | | 264/138 |
| 2015/0152270 | A1* | 6/2015 | Aizenberg | A61L 29/085 |
| | | | | 210/500.27 |

OTHER PUBLICATIONS

Gorissen et al.; Modeling and bonding-free fabrication of flexible fluidic microactuators with a bending motion; publication; 2013; J. Micromech. Microeng. 23045012.

Jungwook Paek et al.; Microsphere-assisted fabrication of high aspect-ratio elastomeric micropillars and waveguides; article; Feb. 14, 2014; 8 pages; Nature Communications | DOI: 10.1038/ncomms4324.

Masashi Ikeuchi et al.; Membrane Micro Emboss (MeME) Process for 3-D Membrane Microdevice; publication; 2009; 15 pages; Intech.

Shuichi Wakimoto et al.; Miniature Pneumatic Curling Rubber Actuator Generating Bidirectional Motion with One Air-Supply Tube; publication; 20 pages; Advanced Robotics 25 (2011) 1311-1330.

Bobak Mosadegh et al.; Pneumatic Networks for Soft Robotics that Actuate Rapidly; publication; 8 pages; Advanced Functional Materials; 2014, 24, 2163-2170.

Ramses V. Martinez et al.; Robotic Tentacles with Three-Dimensional Mobility Based on Flexible Elastomers; publication; 8 pages; Advanced Materials; 2013; 25, 205-212.

Yusaku Watanabe et al.; Small, Soft, and Safe Microactuator for Retinal Pigment Epithelium Transplantation; publication; 4 pages; MEMS 2007, Kobe, Japan, Jan. 21-25, 2007.

Jiwon Lee et al.; Sucrose-based fabrication of 3D-networked, cylindrical microfluidic channels for rapid prototyping of lab-on-a-chip and vaso-mimetic devices; publication; 5 pages; Lab on a Chip; Technical Innovation; The Royal Society of Chemistry 2012.

* cited by examiner

MICROROBOTIC TENTACLES WITH SPIRAL BENDING CAPABILITY BASED ON SHAPE-ENGINEERED ELASTOMERIC MICROTUBES AND METHODS OF MANUFACTURING SAME

CROSS-REFERENCE TO RELATED PATENT APPLICATION

This patent application claims the benefit of U.S. Provisional Patent Application No. 62/251,725, filed Nov. 6, 2015, the entire teachings and disclosure of which are incorporated herein by reference thereto.

STATEMENT REGARDING FEDERALLY SPONSORED RESEARCH AND DEVELOPMENT

This invention was made in part with Government support under Grant Number ECCS0954845 awarded by the National Science Foundation. The Government has certain rights in this invention.

FIELD OF THE INVENTION

This invention generally relates to elastomer-based soft-robots, and more particularly to microrobotic tentacles utilizing elastomeric microtubes.

BACKGROUND OF THE INVENTION

Elastomer-based soft-robots are gaining popularity as safe handlers of delicate objects. For applications like in vivo biomedical manipulation, efforts have been underway for their microscale miniaturization as well but finding efficient actuators for microscale soft-robots remains a difficult task. Pneumatic actuation is a good candidate with its simplicity and efficiency already proven in large-scale soft-robotics, but its microscale implementation entails many technical challenges.

First, current soft-lithographic microfabrication techniques, developed mainly for building planar elastomer structures with low aspect-ratio patterns such as microchannels, are not optimal for constructing three-dimensional, hermetically sealed cavities required for pneumatic actuation. They can still be built by bonding two planar structures or employing dissolvable templates. However, the strength and yield of bonding decrease with the length-scale. Dissolving templates often becomes an equally complex task at microscale. Moreover, large-scale pneumatic actuators rely on many sub-elements, such as surface corrugation or valves, which are neither simple nor desirable to replicate exactly at microscale. In all, a successful microscale realization of a pneumatic soft-actuator requires a combination of new designs and fabrication techniques optimized specifically to that length-scale.

In order to realize the great promise that microscale soft-robots hold as safe handlers of delicate micro-objects and to widen their adoption, such micro-actuators require greater efficiency and ease-of-fabrication. Embodiments of the present invention provide such micro-actuators and methods of fabrication. These and other advantages of the invention, as well as additional inventive features, will be apparent from the description of the invention provided herein.

BRIEF SUMMARY OF THE INVENTION

Embodiments of the present invention provide elastomeric microtube-based pneumatic actuators that can be extended into a microrobotic tentacles and methods of their production. A new, direct peeling-based technique for building long and thin, highly deformable microtubes and a semi-analytical model for their shape-engineering are provided. Using these in combination, the microtube's pneumatically-driven bending is amplified into multi-turn inward spiraling.

In one embodiment, the micro-tentacle exhibit spiraling with the final radius as small as ~185 µm and grabbing force of ~0.78 mN, rendering itself ideal for non-damaging manipulation of soft, fragile micro-objects. This spiraling tentacle-based grabbing modality, the direct peeling-enabled elastomeric microtube fabrication technique, and the concept of microtube shape-engineering of the present invention are all unprecedented and will enrich the field of soft-robotics.

Embodiments of the elastomer-based soft-robotic microtentacles of the present invention are capable of winding around and holding microscale objects. To realize the thin, highly deformable microtubes utilized in such embodiments, new fabrication techniques based on in situ thermal solidification of PDMS dip-coated around a cylindrical template and direct peeling of the cured structure are utilized. Such technique's capability to asymmetrize the microtube's cross-sectional shape enabled the microtube to bend up to a single turn. However, in preferred embodiments the bending is amplified into a life-like, multi-turn spiraling motion. To that end a semi-analytical model is established in another embodiment of the present invention to shape-engineer the microtube to turn it into a micro-tentacle. One embodiment of the optimized micro-tentacle embodiment exhibits a spiraling motion with two full turns and ~200 µm inner radius, which is ideal for grabbing micro-objects.

Experimental confirmation of the feasibility of such a winding motion in elastomer-based microscale pneumatic actuators is also presented. The spiraling capability of embodiments of the present invention will render the micro-tentacle particularly useful for manipulating fragile or easily deformable objects. This is because such spiraling capability will allow embodiments of the micro-tentacle to grab and hold a delicate object either by winding around it conformally or by forming a ring that can scoop up the object without squeezing. Because certain embodiments of the present invention use PDMS for its construction and also to its microorganism-level force, the micro-tentacle is fully compliance-matched to biological structures and will be ideal for future in vivo biomedical manipulation or surgery and endovascular operations where tissue safety holds the highest priority.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1A:
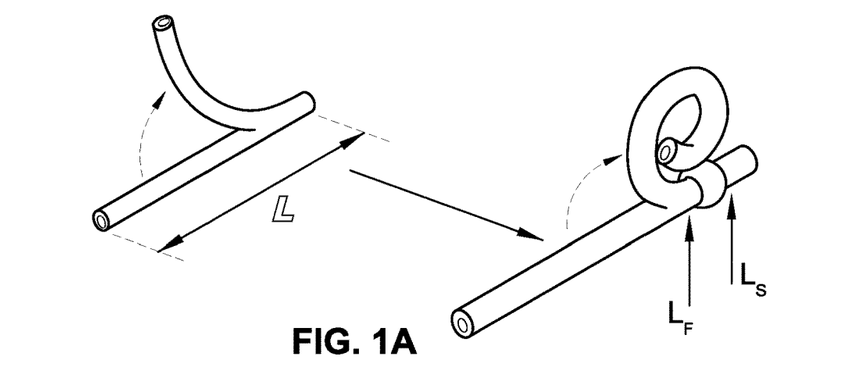
FIGS. 1A-F illustrate embodiments of a microtube tentacle actuator and an embodiment of a method of their manufacture.

Turning now to the drawings, and initially to FIG. 1A, there is illustrated an embodiment of a microtube-type pneumatic soft-actuator that can be extended to microrobotic tentacles in accordance with principles of the present invention. However, as will be recognized by those skilled in the art from the following description, such embodiments are provided by way of example only, not by way of limitation, and that all alternative embodiments are reserved herein.

Spiraling tentacles are widely utilized in nature for grabbing and squeezing objects. While there have been continuous soft-robotic efforts to mimic such spiraling tentacles with pneumatic tube actuators, the life-like, multi-turn spiraling motion has been reproduced only by centimeter-scale tentacles so far. At millimeter and sub-millimeter scales, such tentacles could bend only up to a single-turn or less as shown in the first illustration of FIG. 1A.

However, recognizing that the bending of such small-scale tentacles arises from the mismatch in the elongation levels of the tube's top and bottom sides, embodiments of the present invention have amplified such bending into spiraling through mismatch enhancement. At macroscale, such mismatch enhancement is typically done with bi-elastomeric composite structures or highly modulated surface corrugations. Neither is, however, easy to implement at microscale.

In one embodiment of such mismatch enhancement according to the present invention, as shown in the second illustration of FIG. 1A, the shape-engineered tentacle with a hump produces a tentacle-like spiraling motion. While the following will detail an embodiment of the fabrication technique of the present invention, FIGS. 1B-F illustrate such technique of dip-coating of a cylindrical template with liquid-phase (LP) PDMS shown in FIG. 1B, lifting up of the PDMS-coated template with in situ heating in FIG. 1C, peeling of the cured PDMS microtube with a fiber-optic jacket remover in FIG. 1D (the cross-sectional optical micrograph of a microtube showing the gravity-induced asymmetry ($t_1 \neq t_2$) is included as FIG. 1E), and adding additional structures, such as the mount, endfacet sealing, and hump, to the already completed and tested microtube in FIG. 1F.

As will now be recognized, this embodiment utilizes a two-stepped approach. In the first, easily deformable elastomeric microtubes are fabricated as the platform structure. High deformability is ensured by the thinness of the microtube itself (100-125 μm in inner diameter in preferred embodiments) and its tube-wall (8-32 μm in preferred embodiments). Making such a subtle structure at a length exceeding several millimeters has been deemed unfeasible. However, in accordance with embodiments of the direct peeling-based soft-lithographic technique of the present invention, such fabrication is now possible. Such technique also allows significant asymmetrization of the microtube's cross-sectional shape which leads to bending up to a single-turn (left image of FIG. 1A).

In the second step, shape-engineering is applied to the microtube to amplify the bending into multi-turn spiraling. Using a semi-analytical model, a design rule to be discussed more fully below is established which enables such a spiraling with a simple hump (right image of FIG. 1A).

The outcome is a soft-robotic micro-tentacle that can wind around and hold fragile micro-objects with ~200 μm final spiral radius in one embodiment. This spiraling micro-tentacle manipulator, along with the shape-engineering technique and microtube fabrication technique, are all unprecedented and poised to enrich the field of soft-robotics.

Figures 1B, 1C, 1D:
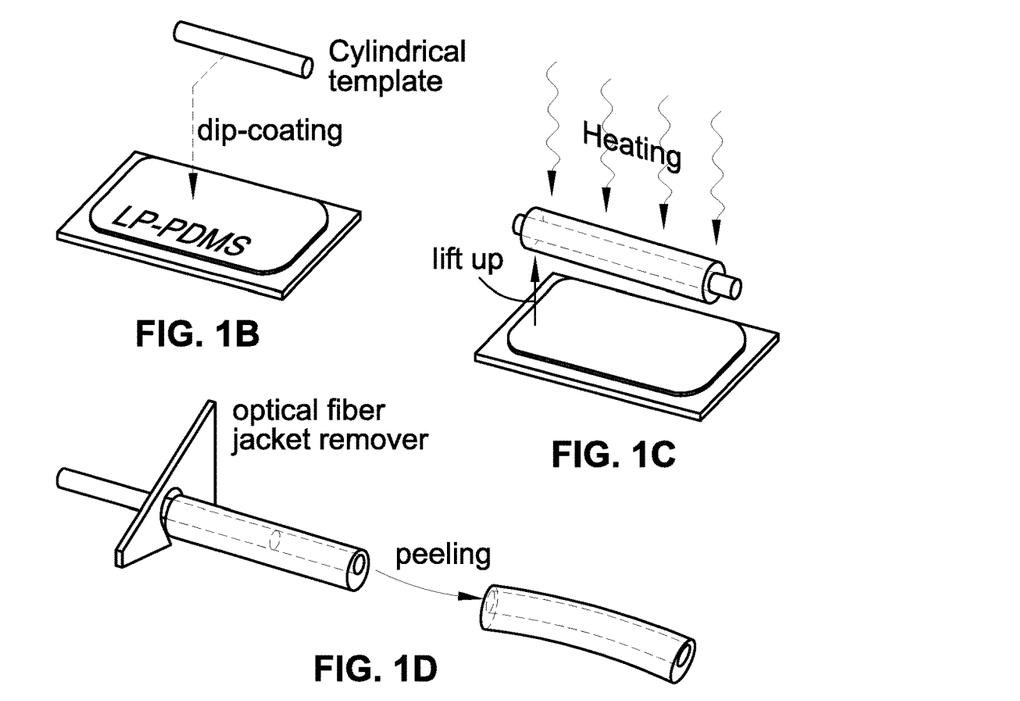
Figure 1E:
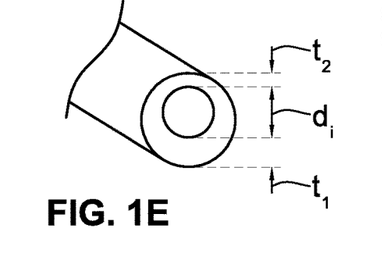

In one embodiment of the method of fabrication of the present invention, as depicted in FIG. 1B, the preparation of the cylindrical template is the first step. Sodium dodecyl sulfate (SDS), a surfactant, was mixed with water at 1:10 weight ratio. Then a cylindrical template was treated with the surfactant solution by dipping it into the mixture for 10 minutes. In various embodiments short sections of ~100 μm-diameter polyamide wire (Stroft ABR) and 125 μm-diameter fused silica optical fiber (SMF-28) were used as the cylindrical template. The former turned out to be better in realizing multi-turn spiraling micro-tentacles with smaller final RoCs when compared with the latter.

In parallel, a thin layer of PDMS was prepared by dispensing a drop of liquid-phase PDMS into a rectangular, 167 μm-deep recess on a glass substrate and removing the excess PDMS with a miniature squeegee. Then, the PDMS thin film was pre-baked with a hot plate set at 70° C. for 8 minutes and left at room temperature for 30 minutes. Upon the completion of pre-baking, the surfactant-treated template was immersed into the PDMS thin film to dip-coat it with PDMS as shown in FIG. 1B.

The PDMS-coated template was then post-baked at 130° C. for 10 minutes in this embodiment as shown in FIG. 1C. During the post-bake, gravity induced the PDMS under baking to flow downward, giving eccentricity to the cross-sectional shape of the PDMS coating. After the post-bake, the PDMS layer was peeled off the template using a standard optical fiber jacket remover (F-STR-103D) as shown in FIG. 1D.

Figure 1F:
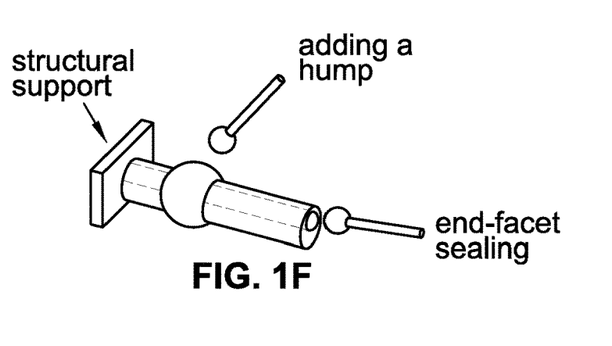

The completed eccentric PDMS microtube (as may be seen in FIG. 1E) was then placed on a pre-made PDMS block, poured liquid-phase PDMS to form the structural support as may be seen from FIG. 1F. The whole assembly was then cured on a hot plate set at 130° C. for 10 minutes. The open-end of the microtube was sealed by dispensing a PDMS droplet. Finally, a 35 nL PDMS droplet was dispensed on the exterior of the microtube to realize the hump structure.

Past reports testify that the biggest issue in using liquid-phase poly(dimethylsiloxane) (LP-PDMS) for building long and thin structures, such as pillars or wires, is its tendency to bead. Previously, the inventors fabricated ultra-high aspect-ratio PDMS micropillars by suppressing the beading with pre-curing and in situ thermal solidification. In accordance with an embodiment of this present invention, the technique is extended to liquid-phase PDMS dip-coated around cylindrical templates to realize PDMS microtubes with very thin walls without bonding.

The completed PDMS microtube is robust enough to be peeled directly from the template with a polymer jacket remover, a standard tool in fiber-optics. This process is simpler, cleaner, and faster than those requiring dissolvable templates, although the use of such is contemplated herein. Using polyamide wires (~100 μm diameter) and glass optical fibers (125 μm diameter) as the template, microtubes with their length L reaching 5-8 mm were fabricated. The main factor limiting L was the inevitable increase in the friction and wrinkling during the peeling process. Despite their high aspect-ratios (typically >50) and thin walls, the microtubes did not sag or collapse, even when no air pressure was applied.

The solidification process can also be controlled for additional tailoring of the microtube's cross-sectional shape. Slowing it down prolongs gravitational impact on the coating, resulting in an increase in the tube's cross-sectional asymmetry. Ten samples that were fabricated with the 100 μm-diameter template exhibited $t_1$ and $t_2$ of 31.8±4.9 (s.d.) and 7.9±1 (s.d.) μm, respectively. The coating thickness can also be made uniform by rotating the template during curing.

As discussed above and shown in FIG. 1F, the microtube can be mounted on another PDMS block or modify its shape. Closing the open end with a drop of liquid-phase PDMS for hermetic sealing is done. A drop can be dispensed at any point along the microtube to form a monolithically integrated hump. This capability was exploited extensively to shape-engineer the microtube.

Figure 2A:
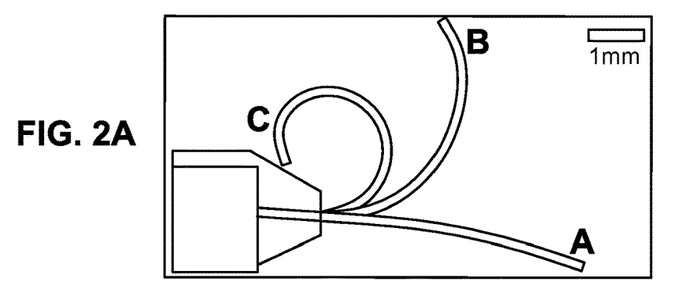
FIGS. 2A-D illustrate pneumatic actuation, axial and radial shape changes observed of embodiments of microtubes constructed in accordance with the method shown in FIG. 1.
Figure 2B:
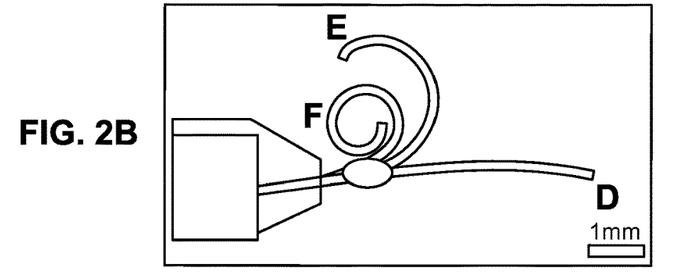
Figure 2C:
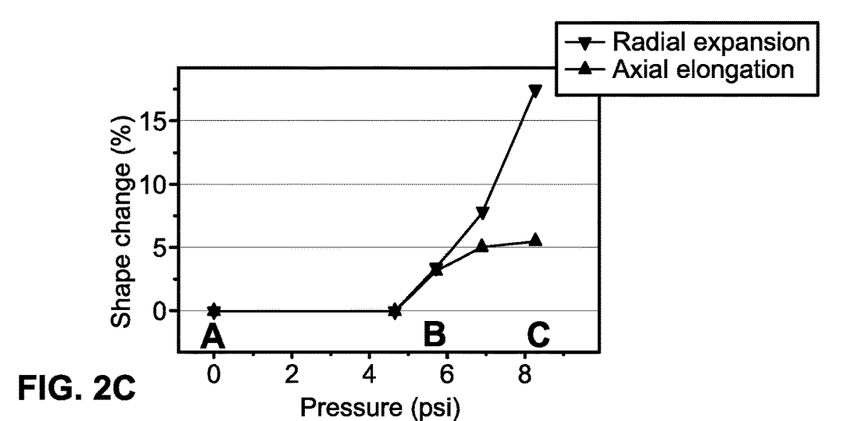
Figure 2D:
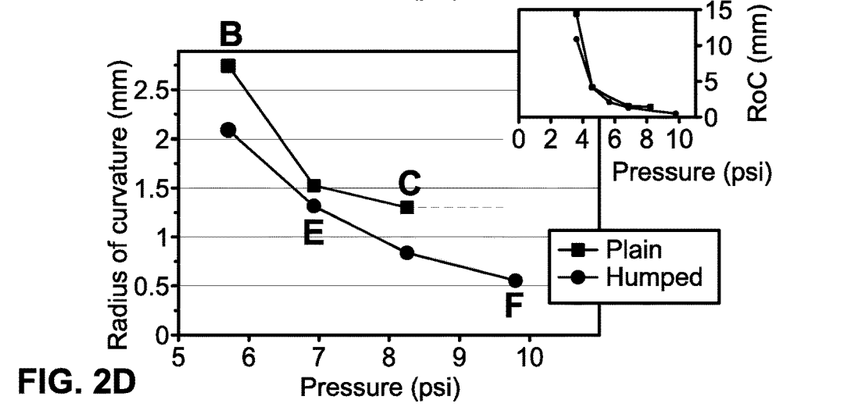

Turning now to FIGS. 2A-D, pneumatic actuation of PDMS microtubes prepared in accordance with embodiments of the present invention is shown in superimposed images of pneumatically actuated PDMS microtube MT1. Labels A-F in FIGS. 2A and 2B indicate pressure levels marked in FIGS. 2C and 2D. The cylinder on the lefthand side of FIGS. 2A and 2B is a blunt syringe needle with 2.108 mm outer diameter. As may be seen from FIG. 2A, before adding a hump, the bending did not develop into spiraling. However, as shown in FIG. 2B the addition of a hump in accordance with embodiments of the present invention at the arrow point amplified MT1's bending into spiraling. (Scale bars: 1 mm). The axial and radial shape changes observed in MT1 (before adding the hump) as a function of pressure is shown in FIG. 2C, and changes in MT1's radius of curvature (RoC) is shown in FIG. 2D. Without the hump, the RoC saturated at ~1.3 mm. The hump reduced the RoC to ~500 μm. As may also been observed, the RoC decreased rapidly once the pressure surpassed the threshold value at ~4.7 psi.

With an understanding of the illustrations of FIGS. 2A-D now at hand, a description of the actual pneumatic actuation of the PDMS microtubes prepared will be given. The microtubes were connected directly to blunt syringe needles for pneumatic actuation. Owing to their high aspect-ratio, thin tube-wall, and inherent softness of PDMS, the microtubes bent significantly upon applying air pressure, as shown in FIGS. 2A and 2B.

As the characterization sample, the one in FIG. 2A (MT1) with L, $d_i$, $t_1$, and $t_2$ at 5600, 104, 35.6, and 7.7 μm, respectively, was used. FIG. 2C shows the levels of its axial elongation and radial expansion at different pressure levels. Clearly, the two morphological changes occurred with a common threshold in the applied pressure (~4.7 psi) below which they became negligible. Beyond the threshold, both the length and radius changed rapidly, eventually getting increased by 5% and 18%, respectively. Such large deformations caused the cross-sectionally asymmetric microtube to bend. FIG. 2D shows the decrease in MT1's radius of curvature (RoC) which also changed abruptly as the pressure surpassed the threshold value. The RoC of MT1 saturated at 1.3 mm at 8.3 psi, forming a ring as shown in FIG. 2A. Other microtubes exhibited similar responses.

Regardless of the pressure or cross-sectional asymmetry, plain microtubes with no cross-sectional change along in the axial direction failed to achieve spiraling. Conventionally, such an insufficient bending has been amplified into spiraling through the use of bi-material composite structures or bellows-like surface corrugations which promote the mismatch in the elongation capabilities. They are, however, very complex to implement at microscale.

Figures 3A, 3B:
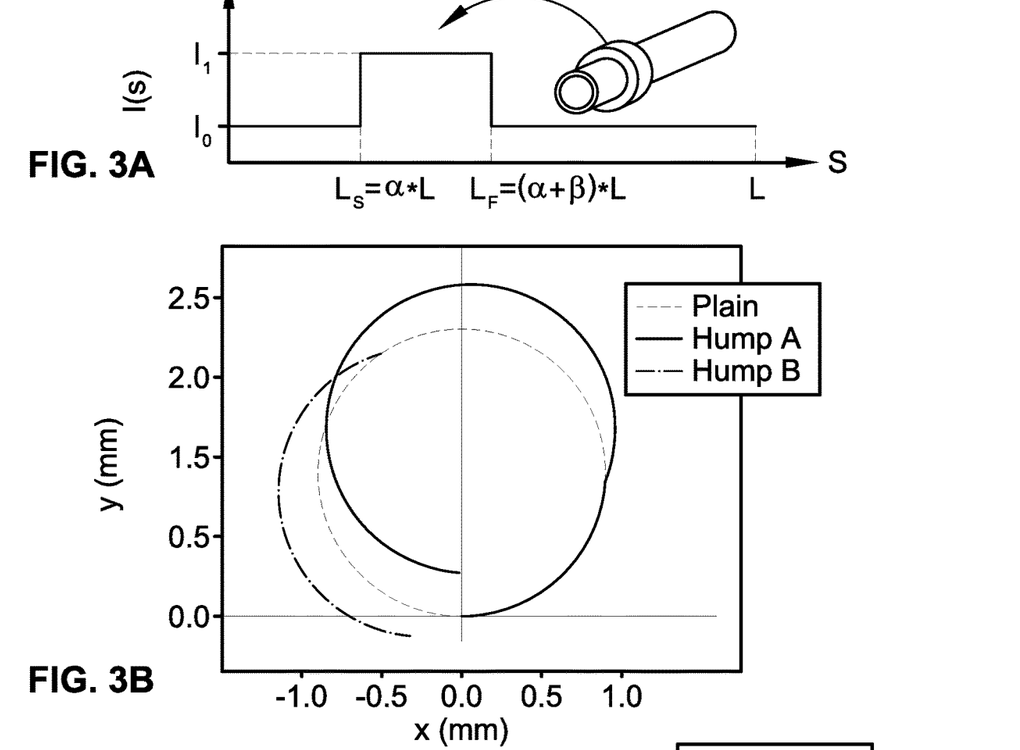
FIGS. 3A-E illustrate shape-engineering principles and results of embodiments of the present invention.
Figure 3C:
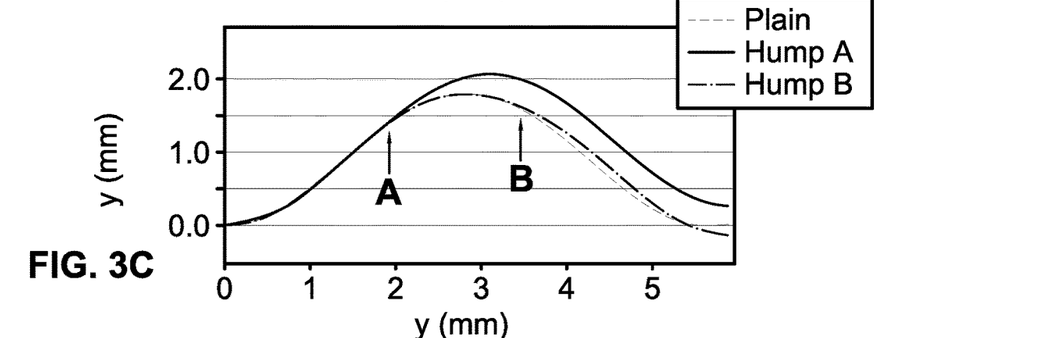
Figure 3D:
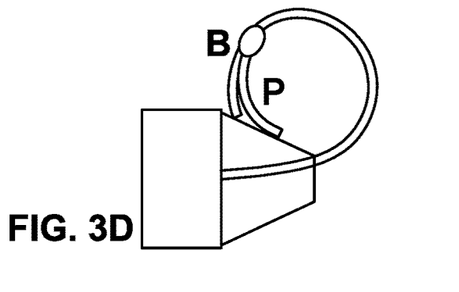
Figure 3E:
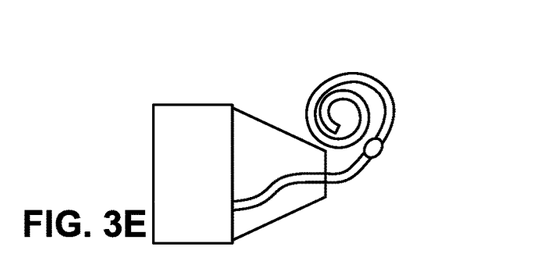

Turning now to FIGS. 3A-3E, the shape-engineering of PDMS micro-tentacles in accordance with embodiments of the present invention will be discussed. FIG. 3A provides a schematic diagram of a humped PDMS micro-tentacle and the change in its I (i.e., second moment of area) due to the hump. Calculated loci (FIG. 3B) and y-values (FIG. 3C) of three microtubes with different hump configurations are shown. In FIGS. 3B and 3C, "Plain" means no axial change in cross-sectional shape, "Hump A" includes a preferred position of the hump ($L_s$=0.21·L), and "Hump B" includes a lesser preferred position of the hump ($L_s$=0.55·L). As may be seen, Hump A re-entered the first quadrant with y>0, achieving an inward spiraling. Hump B, on the other hand, actually rendered the bending worse than that of the non-humped Plain. Overlapped images of microtube actuations before (P) and after (B) installing a non-preferred positioned hump (arrow marked) are shown in FIG. 3D. As may be seen the RoC got bigger even with the hump. Finally, FIG. 3E provides a micrograph of a micro-tentacle with a hump (arrow marked) capable of achieving a 2-turn spiraling with the final RoC of 210 μm constructed in accordance with the teachings of the present invention.

As introduced above, embodiments of the present invention utilize "shape-engineering" to enable tentacle motion. That is, the spiraling motion in the PDMS microtube actuator is enabled by adding a hump to it as discussed above with respect to FIGS. 1F and 2B. In terms of fabrication, this approach is highly advantageous since it requires access only to the microtube's exterior and, hence, can be executed after the microtube is completely fabricated and tested.

Returning specifically to FIG. 2B, the change in MT1's pneumatic actuation after a 610 μm-long, 96 μm-high hump was added is shown. The tentacle clearly exhibited spiraling with the minimum RoC reduced to 500 μm in the illustrated embodiment. The hump's role in promoting the spiraling motion was investigated using the Euler-Bernoulli beam theory.

At the instant when the microtube nearly forms a ring shape, the coordinates (x, y) of the deformed base curve can be described by an integration:

$$u(s) = \int_0^s f\left(\int_0^{s'} \frac{M_0}{E \cdot I(\eta)} d\eta\right) ds' \qquad (1)$$

where $s \in [0, L]$ is the natural coordinate of the beam of length L, and f is a cosine (sine) function for u=x (u=y). E is the material's Young's modulus, and I is the second moment of area.

At this specific instant, it is plausible to assume that a plain microtube has a constant I along its length, and that a humped microtube has a step-wise distribution of I, as shown in FIG. 3A. The bending moment $M_0 = \pi \cdot r^2 \cdot p \cdot d_e$, where r is the radius, p the current pressure, and $d_e$ the distance between the microtube's neutral axis and void hole's center.

FIG. 3B shows that the plain microtube will bend gradually to form a ring but will not achieve spiraling. It is clear from the plot that an inward spiraling requires re-entry of the end-point into the first quadrant with its y>0. In light of the simple harmonic functions in equation (1), the integration over a full cycle will reset both x and y to 0, thereby impeding the desired spiraling.

With the hump, the microtube's geometry can be modulated and, hence, the values of I as shown in FIG. 3A. Considering the step-wise distribution of I, the integration in equation (1) will be split into three, each covering the pre-hump, hump, and post-hump sections as:

$$u(s < L_S) = \int_0^s f\left(\frac{M_0 \cdot s'}{E \cdot I_0}\right) ds' \quad (2)$$

$$u(L_S \leq s < L_F) = \int_0^s f\left(\frac{M_0 \cdot s'}{E \cdot I_1} + \frac{M_0 \alpha L}{E} \cdot \left(\frac{1}{I_0} - \frac{1}{I_1}\right)\right) ds' \quad (3)$$

$$u(L_F \leq s < L) = \int_0^s f\left(\frac{M_0 \cdot s'}{E \cdot I_0} - \frac{M_0 \beta L}{E} \cdot \left(\frac{1}{I_0} - \frac{1}{I_1}\right)\right) ds' \quad (4)$$

where $I_1$ and $I_0$ are the values of I in the hump and non-hump sections, respectively, as shown in FIG. 3A. The position and length of the hump are also specified through $\alpha$ and $\beta$ in FIG. 3A, wherein $\alpha$ is a fraction corresponding to the start position of the hump relative to the length L of the tentacle and $\beta$ is a fraction corresponding to the length of the hump relative to the length L of the tentacle. Equations (2-4) and FIG. 4 shows that the sinusoidal functions in the integrands will obtain abrupt phase shifts when $I_0 < I_1$. By adjusting the levels of the phase-shifts in x and y, the re-entry point can be controlled to the first quadrant. A simple criterion can be derived by assuming $L \cdot \beta (I_1 - I_o)/I_1 \ll L/4$. In that case, spiraling can be ensured with $$\beta \cdot (I_1 - I_o)/(2 \cdot I_1) < \alpha < 0.5 + \beta \cdot (I_1 - I_o)/(2 \cdot I_1) \quad (5)$$

Figure 4A:
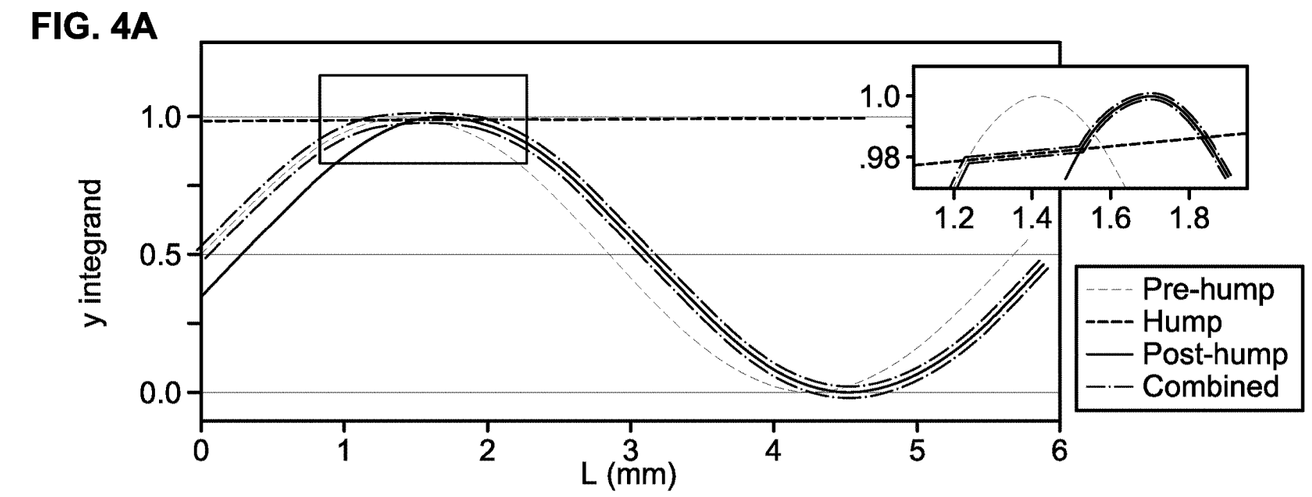
FIGS. 4A-B illustrate that the sinusoidal functions in the integrands in order to obtain abrupt phase shifts for embodiments of the present invention.
Figure 4B:
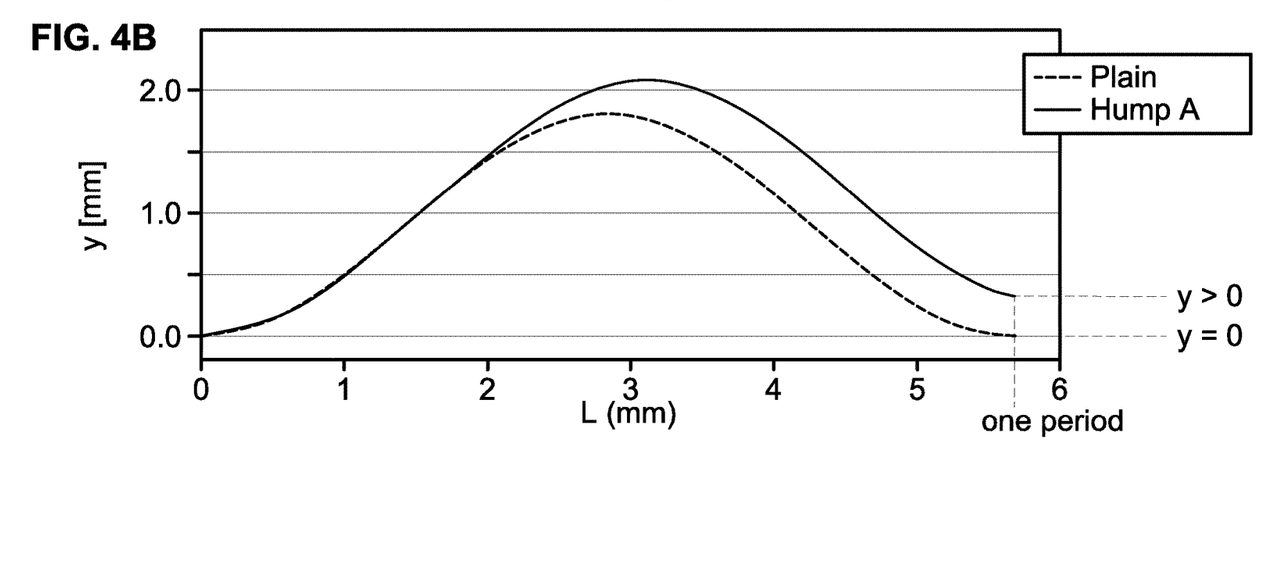

As mentioned above, FIG. 4 illustrates the changes in the integrands due to the hump. Specifically, FIG. 4A illustrates the changes in the y-integrands for the pre-hump, hump, and post-hump sections specified in equations (2)-(4), respectively. For the humped microtube, the integration must be performed along the "combined" route, i.e., first along the pre-hump curve, then the hump curve, and then the post-hump curve. For the un-humped one, it suffices to integrate along the pre-hump curve. FIG. 4B illustrates the integration results for the plain, un-humped microtube and the humped one. For the integration over a full cycle, the purely sinusoidal integrand of the former ended up y=0. In contrast, with $I_1 \gg I_o$, the hump section curve changes much more slowly than those in other sections and can function as a phase-shift between them (as shown in the inset in detail), eventually altering the integration result to a non-zero, positive value. This enables the inward spiraling of the micro-tentacle.

Returning now to FIGS. 3B and 3C, these figures show how a hump (length=0.05·L) affects the level of bending as a function of its position. Using a microtube model with its characteristics approximately matching those of MT1, with $I_0$ and $I_1$ at $5.1 \times 10^{-16}$ and $8.6 \times 10^{-15}$ m$^4$, respectively, the inward spiraling can be obtained when $0.024 < \alpha < 0.524$. The $\alpha$ value of Hump B was set at an non-preferred value of 0.55 while that of Hump A was set to the preferred value of 0.21, as indicated by arrows in FIG. 3C. Despite their identical size and shape, the two humps impacted the microtube's bending very differently. As predicted, Hump A did achieve inward spiraling with the final y>0. Hump B, on the other hand, performed even worse than the plain, un-humped microtube, resulting y<0.

To experimentally confirm the prediction above, another PDMS microtube with structural characteristics very similar to those of MT1 was fabricated with L, $d_i$, $t_1$, and $t_2$ at 5800, 104, 33, and 7.4 μm, respectively, and its bending behaviors were compared before and after adding a hump at a very non-preferred position of 0.78·L. FIG. 3D shows the results. In good agreement with the theoretical prediction, the non-preferred positioned hump resulted in bending radius even greater than that of its non-humped prototype.

FIG. 3E, on the other hand, shows one of the best spiraling results observed so far. As shown in the optical micrograph, the optimized microtube actuator, with L, $d_i$, $t_1$, and $t_2$ at 5470, 105, 34.6, and 8.2 μm, respectively, and its hump installed at 0.17·L point exhibited spiraling with two full turns, achieving the final RoC of 210 μm. RoC as low as 185 μm has been obtained.

Figure 5A:
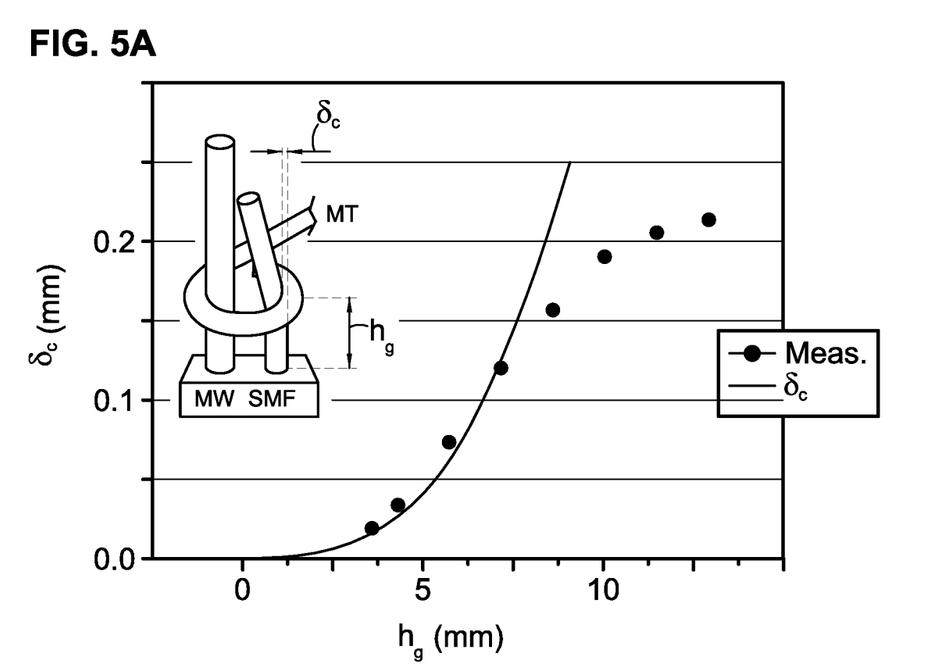
FIGS. 5A-D illustrate characterizations of actuation of embodiments of the micro-tentacle of the present invention.

With the methods of fabrication and hump placement now firmly in hand, the discussion will now turn to characterization of micro-tentacle actuation. As suggested above, the spiral formed by the PDMS micro-tentacle is ideal for grabbing and holding microscale objects. To estimate its grabbing force, the micro-tentacle was configured to deflect a cantilever as shown in the inset of FIG. 5A. As the cantilever, a 15 mm-long section of 125 μm-diameter fused silica optical fiber was used. A rigid, 155 μm-diameter metal wire was also installed in parallel with the fiber. Their surface-to-surface separation was 290 μm. Then, the micro-tentacle was wound around both the metal wire and optical fiber so that its grabbing force can function as a point load at $h_g$ to the optical fiber cantilever. The deflection of the fiber was measured under an optical microscope (E-Zoom6) as the micro-tentacle wound around both the metal wire and optical fiber.

The standard beam deflection theory relates the force F and the deflection $\delta_c$ at $h_g$ as:

$$\delta_c = \frac{F \cdot h_g^3}{3 \cdot E \cdot I} \quad (5)$$

where $I = \pi r^4/4$, r the radius of the optical fiber cantilever, and E the Young's modulus of fused silica. For this measurement, a micro-tentacle with L, $d_i$, $t_1$, and $t_2$ at 5000, 107, 39.1, and 7.2 μm, respectively, was used. Its minimum spiraling diameter was 370 μm and the corresponding maximum achievable deflection $\delta_{c,max}$ was 200 μm. FIG. 5A shows the measured values of $\delta_c$ as a function of $h_g$ at the pressure level of 9.8 psi. Each represents the average of five measurements. The error bar was omitted since the standard deviations were <1% of the average values. The force F, estimated through curve-fitting, was approximately 0.78 mN. Only the first four points were retained in the curve-fitting since $\delta_c$ approached its maximum possible value and began to saturate beyond $h_g \sim 7.5$ mm.

Figure 5B:
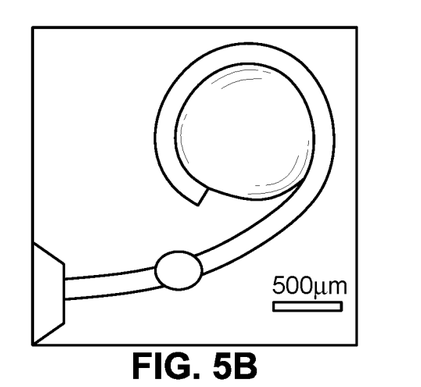
Figure 5C:
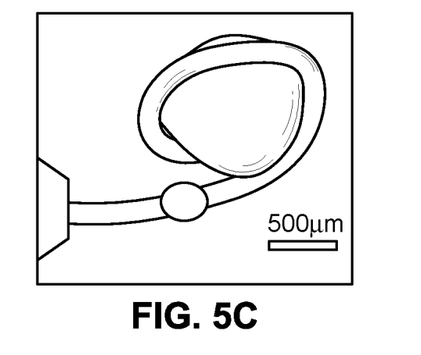
Figure 5D:
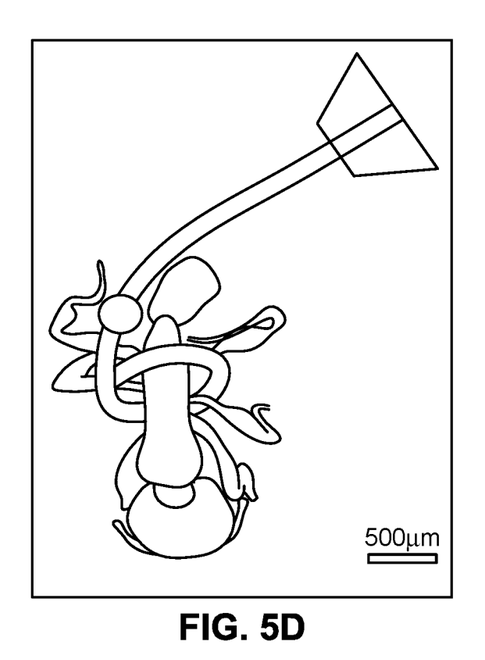

As will now be recognized, the solid line in FIG. 5A represents $\delta_c$, the deflection at the grabbing point ($h_g$), calculated based on the standard beam deflection theory with the point-loaded force of 0.78 mN. The measured $\delta_c$ begins to deviate from the theory after it exceeds 90 μm, the maximum stroke achievable with the current setup. FIGS. 5B and 5C, as will be discussed more fully below, are illustrations based on optical micrographs showing the micro-tentacle's ability to grab and hold a *Mallotus villosus* egg by winding around it conformally. FIG. 5D is an illustration based on an optical micrograph of another micro-tentacle grabbing and holding an ant. (Scale bar: 500 μm for all).

Thanks to the softness of PDMS and the spiraling motion enabled by embodiments of the present invention, the micro-tentacle can function as a soft-robotic grabber of micro-objects that can easily be deformed or damaged under hard material-based grippers. As practical examples shown in FIGS. 5B, 5C, and 5D, biological objects were grabbed. An embodiment of a micro-tentacle with L, $d_r$, $t_1$, and $t_2$ at 5000, 104, 31.5, and 6.9 μm, respectively, was used.

The first target was the egg of *Mallotus villosus* which deforms and bursts easily when manipulated with hard tweezers. Multiple eggs were initially placed on a glass slide and then the micro-tentacle's bending motion was used to separate one egg. Then the egg was grabbed by winding the micro-tentacle around it. The illustrations based on optical micrographs in FIGS. 5B and 5C were obtained while the egg was being held up by the micro-tentacle. In particular, FIG. 5B shows that the micro-tentacle conformally wound itself around the irregularly shaped egg, giving it minimal mechanical stress. No sign of deformation was observed in the released egg. As shown in FIG. 5D, an ant (approximately 400 μm across the waist) was also grabbed and held without damaging its body.

In the experiments discussed above, the cantilever deflection measurement revealed that the spiraling micro-tentacle's grabbing force for the particular embodiment used is in the vicinity of 0.78 mN at 9.8 psi pneumatic pressure. In absolute sense, this force is weaker than those of existing elastomer-based pneumatic micro-actuators. When dealing with microscale actuators, however, their size must be taken into consideration as well. The force-volume ratio of this embodiment of the micro-tentacle is 8.4 mN/mm$^3$ which is higher or comparable to existing elastomer-based pneumatic micro-actuators. This indicates that embodiments of the micro-tentacle of the present invention produced force very efficiently with a simple and small structure. In fact, embodiments of the micro-tentacle of the present invention can be regarded as the bridge between the conventional, larger micro-actuators producing mN-level force and biological micro-organisms such as *C. elegans* capable of producing 62 μN of force. Given that multi-cell aggregates exhibit resilience against force at least up to 1 mN, the sub-mN force level of these embodiments of the micro-tentacle can be highly useful for biomedical cellular manipulation.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of manufacturing a microtube-type pneumatic soft-actuator, comprising the steps of:
   coating a cylindrical template with an elastomer;
   arranging the cylindrical template in a horizontal position;
   forming a gravity-induced eccentricity to a cross-sectional shape of the elastomer on the template;
   removing the elastomer from the template to form a micro-tube;
   sealing one end of the micro-tube.

2. The method of claim 1, further comprising the step of forming a hump structure on the exterior of the micro-tube.

3. The method of claim 1, further comprising the step of applying a surfactant to a surface of the template prior to the step of coating.

4. A method of manufacturing a microtube-type pneumatic soft-actuator, comprising the steps of:
   coating a cylindrical template with an elastomer;
   arranging the cylindrical template in a horizontal position;
   forming a gravity-induced eccentricity to a cross-sectional shape of the elastomer on the template;
   removing the elastomer from the template to form a micro-tube;
   sealing one end of the micro-tube; and
   applying a surfactant to a surface of the template prior to the step of coating;
   wherein the step of applying comprises the steps of:
   mixing sodium dodecyl sulfate (SDS) with water at a 1:10 weight ratio to form a surfactant solution; and
   dipping the template into the surfactant solution for at least approximately 10 minutes.

5. The method of claim 1, wherein the step of coating the template comprises the step of coating an approximately 100 μm-diameter polyamide wire.

6. The method of claim 1, wherein the step of coating the template comprises the step of coating an 125 μm-diameter fused silica optical fiber.

7. A method of manufacturing a microtube-type pneumatic soft-actuator, comprising the steps of:
   coating a cylindrical template with an elastomer;
   arranging the cylindrical template in a horizontal position;
   forming a gravity-induced eccentricity to a cross-sectional shape of the elastomer on the template;
   removing the elastomer from the template to form a micro-tube;

sealing one end of the micro-tube; and
preparing the elastomer prior to the step of coating by the steps of:
dispensing liquid-phase PDMS (LP-PDMS) into a recess on a substrate;
pre-baking the LP-PDMS at approximately 70° C. for approximately 8 minutes; and thereafter
allowing the LP-PDMS to sit at room temperature for approximately 30 minutes.

8. The method of claim 1, wherein the step of coating comprises the step of dip-coating the template.

9. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube; and
sealing one end of the micro-tube;
wherein the step of forming the eccentricity comprises the steps of:
post-baking the elastomer on the template at approximately 130° C. for approximately 10 minutes; and
maintaining the template in the horizontal position during the step of post-baking.

10. The method of claim 9, wherein the step of removing the elastomer from the template is performed after the step of post-baking.

11. The method of claim 1, wherein the step of removing the elastomer from the template comprises the step of peeling the elastomer off of the template.

12. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube; and
sealing one end of the micro-tube;
wherein the step of removing the elastomer from the template comprises the step of peeling the elastomer off of the template;
wherein the step of removing comprises the step of peeling the elastomer from the template using an optical fiber jacket remover.

13. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube; and
sealing one end of the micro-tube;
wherein the step of removing the elastomer from the template comprises the step of dissolving the template.

14. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube;
sealing one end of the micro-tube; and
curing the elastomer at approximately 130° C. for approximately 10 minutes after the step of removing.

15. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube;
sealing one end of the micro-tube; and
forming a hump structure on the exterior of the micro-tube;
wherein the step of forming the hump structure on the exterior of the micro-tube comprises the step of dispensing a 35 nL PDMS droplet on the exterior of the microtube.

16. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube;
sealing one end of the micro-tube; and
forming a hump structure on the exterior of the micro-tube;
wherein the step of forming the hump structure on the exterior of the micro-tube comprises the step of forming the hump structure with a length equal to approximately 0.05 of a total length of the microtube.

17. A method of manufacturing a microtube-type pneumatic soft-actuator, comprising the steps of:
coating a cylindrical template with an elastomer;
arranging the cylindrical template in a horizontal position;
forming a gravity-induced eccentricity to a cross-sectional shape of the elastomer on the template;
removing the elastomer from the template to form a micro-tube;
sealing one end of the micro-tube; and
forming a hump structure on the exterior of the micro-tube;
wherein the step of forming the hump structure on the exterior of the micro-tube comprises the step of forming the hump structure at a position of $L_S=\alpha L$, where L is a length of the microtube and $0.024<\alpha<0.524$.

* * * * *